United States Patent [19]

Tsuruda et al.

[11] Patent Number: 4,661,603

[45] Date of Patent: Apr. 28, 1987

[54] IMIDAZOLE DERIVATIVES

[75] Inventors: Mineo Tsuruda, Fukuoka; Takanori Oe, Nakatsu; Kazuyuki Kawasaki, Buzen; Hiroshi Mikashima, Fukuoka; Hiroshi Yasuda, Nakatsu, all of Japan

[73] Assignee: Yoshitomi Pharmaceutical Industries, Ltd., Osaka, Japan

[21] Appl. No.: 823,633

[22] Filed: Jan. 29, 1986

Related U.S. Application Data

[63] Continuation-in-part of Ser. No. 556,231, Oct. 31, 1983, Pat. No. 4,581,369.

[30] Foreign Application Priority Data

Mar. 3, 1982 [JP] Japan .................................. 57-34365
Jun. 3, 1985 [JP] Japan ................................. 60-121220

[51] Int. Cl.$^4$ .................. C07D 233/60; A61K 31/415
[52] U.S. Cl. .................................................. 548/346
[58] Field of Search ......................... 548/346; 514/399

[56] References Cited

U.S. PATENT DOCUMENTS 4,581,369 4/1986 Tsuruda et al. ................. 548/346 X

*Primary Examiner*—Joseph Paul Brust
*Attorney, Agent, or Firm*—Wenderoth, Lind & Ponack

[57] ABSTRACT

α-(2,6-dimethyl-4-carboxyphenyl)-2-methyl-5-(1-imidazolyl)-benzenemethanol, pharmaceutically acceptable metal salts forms thereof, acid addition salt forms thereof, amino acid addition salt forms thereof, hydrate forms thereof and mixtures thereof.

Such compounds have inhibitory activities on biosynthesis of thromboxane $A_2$, inhibitory activities on platelet aggregation, vasodilative activities and protective effects against liver disorders.

3 Claims, No Drawings

IMIDAZOLE DERIVATIVES

This application is a continuation-in-part of application Ser. No.556,231 filed Oct. 31, 1983, now U.S. Pat. No. 4,581,369 issued 4-8-86.

TECHNICAL FIELD

This invention relates to novel imidazole derivatives, especially α-(2,6-dimethyl-4-carboxyphenyl)-2-methyl-5-(1-imidazolyl)-benzenemethanol, pharmaceutically acceptable metal salts thereof, pharmaceutically acceptable acid addition salts thereof, pharmaceutically acceptable amino acids addition salts thereof, hydrates thereof and mixtures thereof useful as pharmaceuticals, methods for preparing the same and pharmaceutical compositions containing such compound.

DISCLOSURE OF THE INVENTION

Imidazole derivatives of this invention are represented by the formula:

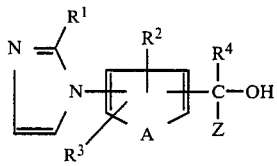
(I)

wherein each of $R^1$ and $R^4$ is a hydrogen atom or a lower alkyl group; each of $R^2$ and $R^3$ is a hydrogen atom, a halogen atom, a hydroxyl group, a lower alkyl group, a lower alkoxy group, an aralkyloxy group, a nitro group or an amino group; A is —O—, —S—, —CH=CH— or —CH=N—; Z is an aryl group, a thienyl group, a pyridyl group or a furyl group, in which definition these aromatic (heterocyclic) rings may have 1 to 3 substituents, each substituent being independently selected from a halogen atom, a lower alkyl group, a cyclic alkyl group, a lower alkoxy group, a hydroxy group, a carboxyl group, a lower alkoxycarbonyl group, a carboxy-lower-alkoxy group, a dilower-alkylamino-lower-alkoxy group and a nitro group.

In the above definitions, the lower alkyl group includes methyl, ethyl, propyl, isopropyl, butyl, isobutyl, sec-butyl and tert-butyl; the cyclic alkyl group includes cyclopropyl and cyclohexyl; the lower alkoxy group includes methoxy, ethoxy, propoxy, isopropoxy and butoxy; the aralkyloxy group includes benzyloxy and phenethyloxy; the lower alkoxycarbonyl group includes methoxycarbonyl, ethoxycarbonyl, propoxycarbonyl, isopropoxycarbonyl and butoxycarbonyl; the carboxy-lower-alkoxy group includes carboxymethoxy, carboxyethoxy, carboxypropoxy and carboxybutoxy; the dilower-alkylamino-lower-alkoxy group includes dimethylaminomethoxy, dimethylaminoethoxy, dimethylaminopropoxy, dimethylaminobutoxy, diethylaminoethoxy, dipropylaminoethoxy and dibutylaminoethoxy; the halogen atom includes fluorine, chlorine, bromine and iodine; the aryl group includes phenyl and naphthyl.

According to this invention, the compounds of formula (I) can be prepared by the following methods, for example:

METHOD 1

This method comprises reacting a compound of the formula:

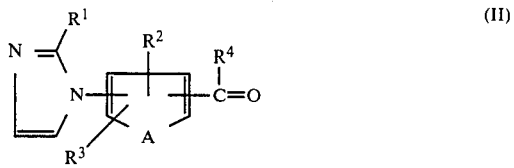
(II)

wherein each symbol is as defined above, with an organometallic compound of the formula [a Grignard reagent (III) or an organolithium compound (IV)]:

ZMgX (III)

or

ZLi (IV)

wherein X is a halogen atom such as chlorine, bromine or iodine and Z is as defined above.

This reaction is carried out in a non-aqueous solvent (e.g. ether, tetrahydrofuran, dioxane, benzene or toluene).

METHOD 2

This method, to be applied for the production of compounds of formula (I) wherein $R^4$ is a hydrogen atom, comprises subjecting a compound of the formula:

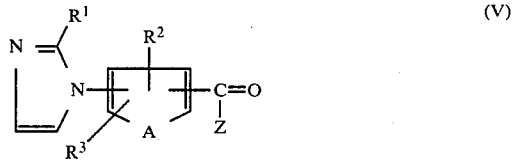
(V)

reduction, wherein each symbol is as defined above.

As a reducing agent can be employed a conventional reagent having the ability to reduce a carbonyl group to the secondary alcohol.

This reaction is carried out by treating a suspension or a solution of the compound of formula (V) in a suitable solvent (e.g. water, methanol, ethanol, dioxane or a mixture thereof) with a complex metal hydride such as sodium borohydride at a temperature of from room temperature to the boiling point of the solvent employed, preferably from room temperature to 100° C., for 1 to 24 hours. This reaction is also carried out by reducing the compound of formula (V) with a complex metal hydride such as lithium aluminum hydride or sodium bis-(2-methoxyethoxy)aluminum hydride in a suitable non-aqueous solvent (e.g. ether, tetrahydrofuran, dioxane or benzene) at a temperature from room temperature to the boiling point of the solvent employed.

METHOD 3

This method, to be applied for the production of compounds of formula (I) where in $R^4$ is a lower alkyl group, comprises reacting the above-mentioned compound of formula (V):

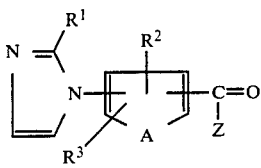

wherein each symbol is as defined above, with a compound of the formula:

$R^5MgX$ (VI)

wherein $R^5$ is a lower alkyl group and X is as defined above.

This reaction is carried out in a non-aqueous solvent (e.g. ether, tetrahydrofuran, dioxane, benzene or toluene).

The starting compounds of formula (V) can be prepared, for example, by the following Method A or Method B:

METHOD A

This method comprises reacting a compound of the formula:

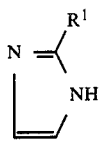

wherein $R^1$ is as defined above, with a compound of the formula:

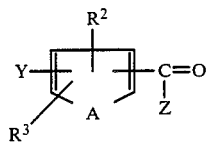

wherein Y is a halogen atom and $R^2$, $R^3$, A and Z are as defined above.

This reaction is generally carried out by treating a metal salt of the compound of formula (VII), which is obtained by treating the compound of formula (VII) with a base (e.g. sodium hydride, sodium amide, a sodium alkoxide such as sodium methoxide or sodium ethoxide, or potassium carbonate) with the compound of formula (VIII) at a temperature of from room temperature to the boiling point of the solvent employed for 1 to 24 hours.

METHOD B

This method comprises reacting a compound of the formula:

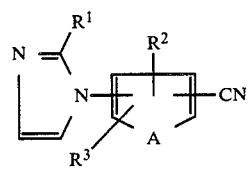

wherein each symbol is as defined above, with the compound of formula (III) or the compound of formula (IV) in a non-aqueous solvent (e.g. ether, tetrahydrofuran, dioxane or benzene), and then subjecting the resulting compound to hydrolysis.

The starting compounds of formula (II) can be prepared by the same method for the production of compounds of formula (V), for example, by the following Method C or Method D.

METHOD C

This method comprises reacting the compound of formula (VII) with a compound of the formula:

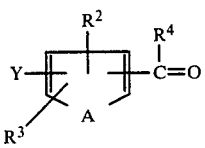

wherein each symbol is as defined above.

This reaction is generally carried out by treating a metal salt of the compound of formula (VII), which is obtained by reacting the compound of formula (VII) with a base (e.g. sodium hydride, sodium amide, a sodium alkoxide such as sodium methoxide or sodium ethoxide or potassium carbonate), with the compound of formula (X) at a temperature of from room temperature to the boiling point of the solvent employed for 1 to 24 hours.

METHOD D

This method, to be applied for the production of compounds of formula (II) wherein $R^3$ is a lower alkyl group, comprises reacting the compound of formula (IX) with the compound of formula (VI), and then subjecting the resulting compound to hydrolysis.

Furthermore, the starting compounds of formulas (VIII) and (X) can easily be prepared in a conventional manner employed in the field of synthetic organic chemistry such as Friedel-Crafts reaction.

The novel imidazole derivatives of formula (I) thus obtained can be converted into pharmaceutically acceptable metal salts, pharmaceutically acceptable acid addition salts and pharmaceutically acceptable amino acids addition salts by treating the compound with alkali metal hydroxides such as sodium hydroxide and potassium hydroxide, alkaline earth metal hydroxides such as calcium hydroxide, inorganic acids such as hydrochloric acid, hydrobromic acid and sulfuric acid, and organic acids such as oxalic acid, fumaric acid, maleic acid, mandelic acid, citric acid, tartaric acid, salicylic acid and amino acids, especially basic amino acids such as arginine, lysine and ornithine, if desired.

The novel imidazole derivatives of the formula (I) may occur as hydrates, as the case may be. Such hydrates are covered by the present invention. Preferred hydrates are hemihydrate to trihydrate, especially hemihydrate, sesquihydrate and monohydrate.

The compounds of formula (I) are present in the form of optical isomers, and this invention embraces all classes of these individual isomers and the mixtures thereof. When the resolution of racemic compounds is necessary, conventional manners such as fractional crystallizations and various chromatographic techniques are available.

The imidazole derivatives of formula (I) and acid addition salts thereof have pharmacological activities such as inhibitory activities on biosynthesis of thromboxane $A_2$, inhibitory activities on platelet aggregation or vasodilative activities, and these compounds are useful for the prophylaxis or the therapy of thrombosis, cerebral apoplexy, myocardial infarction, acute heart death, angina pectoris, hypertention, asthma or nephritis.

Furthermore, the compounds of this invention exhibit potent protective effects against animal liver disorders induced by carbon tetrachloride, and are useful for treating hepatic insufficiencies such as acute and chronic hepatitis, hepatocirrihosis, fatty liver or toxic hepatitis induced by ethanol, an organophosphorus insecticide, chloroform or carbon tetrachloride.

The following experimental data demonstrate the pharmaceutical utilities of the compounds of this invention.

(1) The inhibitory activities on platelet aggregation

According to the method described in Journal of Physiology, vol. 162, page 67 (1962), the inhibitory activities of compounds of this invention on platelet aggregation were measured from the changes in transmittance with an aggregometer (Rikadenki Electronics Co., Japan).

Before and one hour after the oral administration of test compounds to rabbits, blood was collected. The blood was mixed with sodium citrate in the ratio of 9:1 by volume. Platelet rich plasma (PRP) was prepared by centrifuging the citrated blood at 1000 rpm for 10 minutes, and platelet poor plasma (PPP), by centrifuging the remaining citrated blood at 3000 rpm for 10 minutes.

The transmittance of aggregometer was adjusted to 0 and 100% with PRP and PPP, respectively. To 0.3 ml of a PRP sample was added 0.003 ml of arachidonic acid solution. The changes in transmittance of the mixture were measured using the aggregometer with stirring at 1200 rpm.

Inhibitory activities on platelet aggregation were assessed as % inhibition by comparing the rate of aggregation of treated PRP with that of blood collected before the oral administration of test compounds. The results are summarized in Table 1.

TABLE 1

| Test compound | Inhibitory activities on platelet aggregation | |
|---|---|---|
| | Dose (mg/kg) | Rate of inhibition (%) |
| α-(2,4,6-Trimethylphenyl)-3-chloro-4-(1-imidazolyl)-benzenemethanol | 10 | 80 |
| α-(2,4,6-Trimethylphenyl)-3-(1-imidazolyl)benzenemethanol | 10 | 100 |
| α-(2,4,6-Trimethylphenyl)-2-methyl-3-(1-imidazolyl)-benzenemethanol | 10 | 68 |
| α-(2,4,6-Trimethylphenyl)-4-methyl-3-(1-imidazolyl)-benzenemethanol | 10 | 88 |
| α-(2,4,6-Trimethylphenyl)-2-chloro-5-(1-imidazolyl)-benzenemethanol | 10 | 71 |
| α-(2,4,6-Trimethylphenyl)-2-methyl-5-(1-imidazolyl)-benzenemethanol | 10 | 100 |
| α-(2,6-Dimethyl-4-carboxyphenyl)-2-methyl-5-(1-imidazolyl)benzenemethanol | 10 | 100 |
| α-(2,6-Dimethyl-4-carboxyphenyl)-2-chloro-5-(1-imidazolyl)benzenemethanol | 10 | 100 |
| α-(2,6-Dimethyl-4-ethoxycarbonylphenyl)-2-methyl-5-(1-imidazolyl)-benzenemethanol | 10 | 100 |
| α-(2,6-Dimethyl-4-isopropoxycarbonylphenyl)-2-methyl-5-(1-imdazolyl)-benzenemethanol | 10 | 76 |
| α-(2,6-Dimethyl-4-methoxycarbonylphenyl)-2-methyl-5-(1-imidazolyl)-benzenemethanol | 10 | 100 |

(2) Effect on arachidonic acid metabolism

Effects of test compounds on thromboxane synthetase, cyclo-oxygenase and prostacyclin synthetase were examined in vitro by the following methods:

(a) Inhibitory effect on thromboxane synthetase

According to the method described in Journal of Biological Chemistry, vol. 252, page 5871 (1977), thromboxane was produced by incubating human platelet microsomes with 4.3 μM $^{14}$C-arachidonic acid at 25° C. for 5 minutes. Since thromboxane $A_2$ is extremely short-lived, thromboxane $B_2$, which is a stable degradation product of thromboxane $A_2$, was assayed. The incubation mixture was extracted with ethyl acetate, and thromboxane $B_2$ was separated on a thin-layer chromatogram. The zone of thromboxane $B_2$ on a silica gel plate was detected with a radiochromatoscanner and scraped off. The radioactivities were determined with a liquid scintilation counter.

The inhibitory activities of test compounds on thromboxane synthetase were assessed by comparing the contents of thromboxane formed in the presence and the absence of test compounds.

The results are summarized in Table 2.

(b) Inhibitory effect on cyclo-oxygenase

According to the method described in Proceedings of National Academy of Sciences, U.S.A., vol. 71, page 3645 (1974), bovine seminal vesicle microsomes were incubated with 104.3 μM $^{14}$C-arachidonic acid at 25° C. for 10 minutes. Prostaglandin $E_2$ thus formed was separated and assayed using the same method as (a).

The inhibitory activities of test compounds on cyclo-oxygenase were assessed by comparing the contents of prostaglandin $E_2$ formed in the presence and absence of test compounds.

The results are summarized in Table 2.

(c) Inhibitory effect on prostacyclin synthetase

According to the method described in Journal of Pharmacology and Experimental Therapeutics, vol. 215, page 240 (1980), prostacyclin was formed by incubating the rat arota ring with 1.7 μM $^{14}$C-arachidonic acid at 37° C. for 20 minutes. Since prostacyclin is extremely short-lived, 6-keto-prostaglandin $F_{1\alpha}$, which is a stable degradation product of prostacyclin, was separated and assayed using the same method as (a).

The inhibitory activities of test compounds on prostacyclin synthetase were assessed by comparing the contents of 6-keto-prostaglandin $F_{1\alpha}$ formed in the presence and the absence of test compounds.

The results are summarized in Table 2.

TABLE 2

| Test compound | Effect on arachidonic acid metabolism (50% inhibitory molar concentration) | | |
|---|---|---|---|
| | Inhibitory effect on thromboxane synthetase | Inhibitory effect on cyclooxygenase | Inhibitory effect on prostacyclin synthetase |
| α-(2,4,6-Trimethylphenyl)-3-chloro-4-(1-imidazolyl)-benzenemethanol | $1.8 \times 10^{-7}$ | $>10^{-4}$ | $>10^{-4}$ |
| α-(2,4,6-Trimethylphenyl)-3-(1-imidazolyl)benzene-methanol | $3.4 \times 10^{-7}$ | $>10^{-3}$ | $>10^{-4}$ |
| α-(2,4,6-Trimethylphenyl)-2-chloro-5-(1-imidazolyl)-benzenemethanol | $2.3 \times 10^{-6}$ | $>10^{-3}$ | $>10^{-3}$ |
| α-(2,4,6-Trimethylphenyl)-2-methyl-5-(1-imidazolyl)-benzenemethanol | $8.2 \times 10^{-7}$ | Not tested | Not tested |
| α-(2,6-Dimethyl-4-carboxyphenyl)-2-methyl-5-(1-imidazolyl)benzenemethanol | $2.2 \times 10^{-8}$ | $>10^{-4}$ | $>10^{-4}$ |
| α-(2,6-Dimethyl-4-carboxyphenyl)-2-chloro-5-(1-imidazolyl)benzenemethanol | $5.2 \times 10^{-8}$ | $>10^{-4}$ | $>10^{-4}$ |
| α-(2,6-Dimethyl-4-ethoxycarbonylphenyl)-2-methyl-5-(1-imidazolyl)-benzenemethanol | Not tested | $>10^{-4}$ | $>10^{-4}$ |
| α-(2,6-Dimethyl-4-isopropoxycarbonylphenyl)-2-methyl-5-(1-imidazolyl)-benzenemethanol | Not tested | $>10^{-4}$ | $>10^{-4}$ |
| α-(2,6-Dimethyl-4-methoxycarbonylphenyl)-2-methyl-5-(1-imidazolyl)-benzenemethanol | $7.0 \times 10^{-7}$ | $>10^{-4}$ | $>10^{-4}$ |

(3) Acute toxicity

According to the method described in Journal of Pharmacological and Experimental Therapeutics, vol. 96, page 99 (1949), the test compounds were orally administered to a group consisting of six male Wistar rats. The 50% lethal doses ($LD_{50}$, mg/kg) were determined. The results are summarized in Table 3.

TABLE 3

| Test compound | $LD_{50}$ (mg/kg, p.o.) |
|---|---|
| α-(2,4,6-Trimethylphenyl)-3-chloro-4-(1-imidazolyl)benzenemethanol | >1,000 |
| α-(2,4,6-Trimethylphenyl)-3-(1-imidazolyl)benzenemethanol | >1,000 |
| α-(2,4,6-Trimethylphenyl)-2-methyl-3-(1-imidazolyl)benzenemethanol | >1,000 |
| α-(2,4,6-Trimethylphenyl)-4-methyl-3-(1-imidazolyl)benzenemethanol | >1,000 |
| α-(2,4,6-Trimethylphenyl)-2-chloro-5-(1-imidazolyl)benzenemethanol | >1,000 |
| α-(2,4,6-Trimethylphenyl)-2-methyl-5-(1-imidazolyl)benzenemethanol | >1,000 |
| α-(2,6-Dimethyl-4-carboxyphenyl)-2-methyl-5-(1-imidazolyl)benzenemethanol | >1,000 |
| α-(2,6-Dimethyl-4-carboxyphenyl)-2-chloro-5-(1-imidazolyl)benzenemethanol | >1,000 |
| α-(2,6-Dimethyl-4-ethoxycarbonylphenyl)-2-methyl-5-(1-imidazolyl)benzenemethanol | >1,000 |
| α-(2,6-Dimethyl-4-isopropoxycarbonylphenyl)-2-methyl-5-(1-imidazolyl)benzenemethanol | >1,000 |
| α-(2,6-Dimethyl-4-methoxycarbonylphenyl)-2-methyl-5-(1-imidazolyl)benzenemethanol | >1,000 |

When the compounds of this invention are used as medicines, they may be administered orally or parenterally in the form of tablets, capsules, granules, powder or injectable solutions by mixing with a pharmacologically acceptable carrier, excipient or diluent.

The dose may vary depending upon the disease to be treated or the conditions of the patients to be treated, but the daily dose preferably ranges from 0.01 to 50 mg per Kg of human body weight, in 1 to 4 divided doses.

The present invention will be more concretely explained by the following working and reference examples, but they should not be thought to limit the scope of the invention.

REFERENCE EXAMPLE 1

A Grignard reagent which is prepared by reacting 1.9 g of magnesium with 15 g of p-chlorobromobenzene in 150 ml of anhydrous ether is added to a suspension of 10.2 g of 3-cyano-2-(1-imidazolyl)pyridine in 200 ml of benzene at 30°–35° C. After the addition is complete, the whole mixture is stirred at room temperature for 1.5 hours. The reaction mixture is treated with an aqueous ammonium chloride solution under ice cooling. To the benzene layer containing the resulting 3-(4-chlorobenzimidoyl)-2-(1-imidazolyl)pyridine is added dilute hydrochloric acid and the mixture is stirred at 35° C. for 10 minutes for hydrolysis. The dilute hydrochloric acid layer is separated and made alkaline with sodium hydroxide and then extracted with chloroform. The chloroform layer is washed with water, dried and concentrated to give 3-(4-chlorobenzoyl)-2-(1-imidazolyl)pyridine as an oil in high yield. This oily product can be used in the next reaction without isolation, but when the oil is treated with toluene, crystallization takes place. Upon recrystallization from toluene the product is obtained as white crystals, melting at 118°–120° C.

REFERENCE EXAMPLE 2

To a suspension of 13 g of sodium hydride (60% dispersion in mineral oil) in 240 ml of dimethylformamide is added 20 g of imidazole over a 15 minute period under occasional ice cooling. After the mixture is stirred at room temperature for an hour, 60 g of 2-chloro-5-(4-chlorobenzoyl)pyridine is added. The whole mixture is heated to 35° C. and an exothermic reaction starts. When the temperature rises at 60° C., the mixture is ice-cooled and then stirred at room temperature for an hour. The reaction mixture is poured into ice-cold water, the crystals precipitated are filtered off and recrystallized from ethanol to give 58 g of 5-(4-chlorobenzoyl)-2-(1-imidazolyl)pyridine as white crystals, melting at 155°–156° C.

REFERENCE EXAMPLE 3

To a suspension of 2.9 g of sodium hydride (60% dispersion in mineral oil) in 50 ml of hexamethylphosphoric triamide is added 5.3 g of imidazole over a 30 minute period under heating at 40° C. After the addition is complete, the mixture is stirred at room temperature for an hour. To the reaction mixture is added 16.6 g of 3-fluoro-2',4',6'-trimethylbenzophenone and the mixture is stirred at 70° C. for 24 hours. The reaction solution is poured into ice-cold water and extracted with ethyl acetate. The ethyl acetate layer is washed with water, dried and concentrated. The residue is recrystallized from a mixture of toluene and isopropyl ether to give 16 g of 3-(1-imidazolyl)-2',4',6'-trimethylbenzophenone as white crystals, melting at 134°–136° C.

REFERENCE EXAMPLE 4

To a suspension of 2.3 g of sodium hydride (60% dispersion in mineral oil) in 50 ml of dimethylformamide is added 4.2 g of imidazole over a 5 minute period under occasional ice cooling. After stirring at room temperature for 30 minutes, a solution of 14.2 g of 3-chloro-4-fluoro-2',4',6'-trimethylbenzophenone in 10 ml of dimethylformamide is added and the mixture is stirred at 50° C. for 3 hours. The reaction mixture is poured into ice-cold water and extracted with benzene. After benzene is distilled off, the residue is purified column-chromatographically to give 15.6 g of 3-chloro-4-(1-imidazolyl)-2',4',6'-trimethylbenzophenone as a colorless oil.

EXAMPLE 1

To a suspension of 16 g of 3-(1-imidazolyl)-2',4',6'-trimethylbenzophenone in 90 ml of ethanol is added a solution of 3.4 g of sodium borohydride in 30 ml of water. After stirring at 56° C. for 20 hours, the reaction mixture is poured into ice-cold water. The precipitate is filtered off and recrystallized from a mixture of dioxane and water to give 13.6 g of α-(2,4,6-trimethylphenyl)-3-(1-imidazolyl)benzenemethanol as white crystals, melting at 191°–193° C.

EXAMPLE 2

In 100 ml of ethanol is dissolved 15.6 g of oily 3-chloro-4-(1-imidazolyl)-2',4',6'-trimethylbenzophenone obtained in the reference example 4. To the ethanol solution is added a solution of 1.8 g of sodium borohydride in 20 ml of water. After the whole solution is stirred at 50° C. for 17 hours, the reaction mixture is poured into ice-cold water and extracted with chloroform. The chloroform is distilled off and the residue is recrystallized from toluene to give 14 g of α-(2,4,6-trimethylphenyl)-3-chloro-4-(1-imidazolyl)benzenemethanol as white crystals, melting at 156°–157° C.

EXAMPLE 3

To a suspension of 10.9 g of 2-chloro-5-(1-imidazolyl)-2',4',6'-trimethylbenzophenone in 65 ml of ethanol is added a solution of 1.4 g of sodium borohydride in 4 ml of water. The mixture is stirred at 50° C. for 18 hours, and then the reaction mixture is poured into ice-cold water. The crystals precipitated are filtered off and recrystallized from ethanol to give 9.4 g of α-(2,4,6-trimethylphenyl)-2-chloro-5-(1-imidazolyl)benzenemethanol as white crystals, melting at 206°–207° C.

EXAMPLE 4

To a suspension of 7.3 g of 2-methyl-5-(1-imidazolyl)-2',4',6'-trimethylbenzophenone is 50 ml of ethanol is added a solution of 1 g of sodium borohydride in 10 ml of water. After the mixture is stirred at 50° C. for 10 hours, the reaction mixture is poured into ice-cold water. The crystals precipitated are filtered off and recrystallized from ethanol to give 5.8 g of α-(2,4,6-trimethylphenyl)-2-methyl-5-(1-imidazolyl)benzenemethanol as white crystals, melting at 190°–191° C.

EXAMPLE 5

To a suspension of 4 g of 2-methoxy-5-(1-imidazolyl)-2',4',6'-trimethylbenzophenone in 20 ml of ethanol is added a solution of 0.9 g of sodium borohydride in 5 ml of water. After the whole mixture is stirred at 70°–75° C. for 1.5 hours, the reaction mixture is poured into ice-cold water. The crystals precipitated are filtered off and recrystallized from ethanol to give 2.9 g of α-(2,4,6-trimethylphenyl)-2-methoxy-5-(1-imidazolyl)benzenemethanol as white crystals, melting at 187°–188° C.

EXAMPLE 6

A Grignard reagent which is prepared by reacting 1.9 g of magnesium with 15 g of p-chlorobromobenzene in 40 ml of ether is added to a suspension of 6.2 g of 4-(1-imidazolyl)benzaldehyde in 70 ml of ether at 0° C. After the mixture is stirred at room temperature for an hour, the reaction mixture is poured into an aqueous ammonium chloride solution with caution. The mixture is extracted with chloroform and the chloroform is distilled off. The residue is purified column-chromatographically and recrystallized from toluene to give 8.6 g of α-(4-chlorophenyl)-4-(1-imidazolyl)benzenemethanol as white crystals, melting at 148.5°–149.5° C.

EXAMPLE 7

To a solution of 4.8 g of 3-(4-chlorobenzoyl)-2-(1-imidazolyl)pyridine in 35 ml of ethanol and 5 ml of water is added 0.64 g of sodium borohydride. After the mixture is stirred at room temperature for an hour, the reaction mixture is poured into water and extracted with chloroform. The chloroform is distilled off and the residue is recrystallized from toluene to give 4.3 g of α-(4-chlorophenyl)-2-(1-imidazolyl)-3-pyridinemethanol as white crystals, melting at 133°–134° C.

EXAMPLE 8

To a solution of 7 g of 5-(4-chlorobenzoyl)-2-(1-imidazolyl)pyridine in 60 ml of ethanol plus 10 ml of water is added 1 g of sodium borohydride. After the mixture is stirred at room temperature for an hour, the solvent is distilled off. To the residue is added water and the mixture is extracted with chloroform. After the chloroform is distilled off, the residue is recrystallized from a mixture of toluene and ethanol to give 6.5 g of α-(4-chlorophenyl)-2-(1-imidazolyl)-5-pyridinemethanol as white crystals, melting at 147°–149° C.

EXAMPLE 9

A Grignard reagent which is prepared by reacting 0.46 g of magnesium with 3 g of methyl iodide in 30 ml of ether is added to a suspension of 4.5 g of 2-(1-imidazolyl)-5-(4-chlorobenzoyl)pyridine in 50 ml of ether at −5° C. After the mixture is stirred at room temperature for an hour, the reaction mixture is poured into an aqueous ammonium chloride solution with caution. The precipitate is extracted with chloroform and the chloroform is distilled off. The residue is recrystallized from toluene to give 4.1 g of 1-[2-(1-imidazolyl)-5-pyridyl]-1-(4-chlorophenyl)ethanol in 90.3% yields as white crystals, melting at 140°–142° C.

The following compounds can be prepared in a similar manner mentioned in the above Examples:

(10) α-(2,4,6-Trimethylphenyl)-2-methyl-3-(1-imidazolyl)benzenemethanol, melting at 221°–222° C.
(11) α-(2,4,6-Trimethylphenyl)-4-methyl-3-(1-imidazolyl)benzenemethanol, melting at 132°–133° C.
(12) α-(2,4,6-Trimethylphenyl)-3-chloro-5-(1-imidazolyl)benzenemethanol, melting at 194°–196° C.
(13) α-(2,4,6-Trimethylphenyl)2-hydroxy-5-(1-imidazolyl)benzenemethanol, melting at 188°–189° C. (decomposition)

(14) α-(4-Chlorophenyl)-3-nitro-4-(1-imidazolyl) benzenemethanol, semi-solid

| Elementary analysis: | | | |
|---|---|---|---|
| | C (%) | H (%) | N (%) |
| Found: | 58.31 | 3.63 | 12.83 |
| Calculated: | 58.28 | 3.67 | 12.74 |

(15) α-(2-Chlorophenyl)-4-(1-imidazolyl)benzenemethanol hydrochloride, melting at 212°14 214° C.

(16) α-(2,4,6-Trimethylphenyl)-4-(1-imidazolyl) benzenemethanol, melting at 155°–157° C., its hydrochloride, melting at 234°–235° C. (decomposition)

(17) α-(4-Chlorophenyl)-3-amino-4-(1-imidazolyl) benzenemethanol, melting at 202°–203° C.

(18) α-(4-Nitrophenyl)-4-(1-imidazolyl)benzenemethanol, melting at 176°–178° C.

(19) α-(4-Chlorophenyl)-3-methyl-4-(1-imidazolyl)benzenemethanol, melting at 144°–145° C.

(20) α-(2,4,6-Trimethylphenyl)-3-methyl-4-(1-imidazolyl)benzenemethanol, melting at 80°–100° C.

(21) α-Phenyl-3-(1-imidazolyl)benzenemethanol, melting at 110°–112° C.

(22) α-(4-Methylphenyl)-3-(1-imidazolyl)benzenemethanol, melting at 131°–133° C.

(23) α-(2-Methoxy-5-methylphenyl)-3-(1-imidazolyl)benzenemethanol, melting at 127°–128° C.

(24) α-(2-Methylphenyl)-4-methoxy-3-(1-imidazolyl)benzenemethanol, a colorless oily product; NMR (CDCl$_3$) δ(ppm): 2.20 (s, 3H, —C$_6$H$_4$—CH$_3$), 3.72 (s, 3H, O—CH$_3$)

(25) α-(2,4,6-Trimethylphenyl)-2-(1-imidazolyl)benzenemethanol, melting at 201°–203° C.

(26) α-(2,4,6-Trimethylphenyl)-2-chloro-4-(1-imidazolyl)benzenemethanol, melting at 154°–156° C.

(27) α-(2-Thienyl)-3-(1-imidazolyl)benzenemethanol, melting at 107°–109° C.

(28) α-(2-Methoxy-3-pyridyl)-4-(1-imidazolyl)benzenemethanol, melting at 162°–164° C.

(29) α-(2-Furyl)-4-(1-imidazolyl)benzenemethanol, melting at 136°–138° C.

(30) α-(2-Thienyl)-2-(1-imidazolyl)benzenemethanol, melting at 143°–144° C.

(31) α-(2-Thienyl)-2-(2-methyl-1-imidazolyl)benzenemethanol, melting at 134°–136° C.

(32) α-(3-Carboxyphenyl)-3-(1-imidazolyl)benzenemethanol, melting at 162°–164° C.

(33) α-(2,4,6-Trimethylphenyl)-5-chloro-2-(1-imidazolyl)benzenemethanol, melting at 190°–192° C.

(34) α-(4-tert-Butyl-2,6-dimethylphenyl)-2-chloro-5-(1-imidazolyl)benzenemethanol, melting at 171°–173° C.

(35) α-(2,4,6-Trimethylphenyl)-3-amino-5-(1-imidazolyl)benzenemethanol, melting at 205°–207° C.

(36) α-(2,4,6-Trimethylphenyl)-3-methoxy-5-(1-imidazolyl)benzenemethanol, melting at 149°–151° C.

(37) α-(2,4,6-Trimethylphenyl)-2-isopropoxy-5-(1-imidazolyl)benzenemethanol, melting at 167°–168° C.

(38) α-(2,4,6-Trimethylphenyl)-4-methoxy-3-(1-imidazolyl)benzenemethanol, melting at 118°–119° C.

(39) α-(2,4,6-Trimethylphenyl)-4-isopropoxy-3-(1-imidazolyl)benzenemethanol, melting at 167°–168° C.

(40) α-(2,4,6-Trimethylphenyl)-4-hydroxy-3-(1-imidazolyl)benzenemethanol, melting at 205°–206° C. (decomposition)

(41) α-(2,4,6-Trimethylphenyl)-4-benzyloxy-3-(1-imidazolyl)benzenemethanol, melting at 186°–187° C.

(42) α-(2,4,6-Trimethylphenyl)-2-benzyloxy-5-(1-imidazolyl)benzenemethanol, melting at 189°–190° C.

(43) α-(3,5-Di-tert-butyl-4-hydroxyphenyl)-3-(1-imidazolyl)benzenemethanol

(44) α-(2,4,6-Trimethylphenyl)-3-nitro-5-(1-imidazolyl)benzenemethanol

(45) α-(2,4,6-Trimethylphenyl)-2-nitro-5-(1-imidazolyl)benzenemethanol

(46) α-(2,4,6-Trimethylphenyl)-3-bromo-5-(1-imidazolyl)benzenemethanol

(47) α-(2,4,6-Trimethylphenyl)-2-chloro-3-(1-imidazolyl)benzenemethanol

(48) α-(2,4,6-Trimethylphenyl)-4-chloro-3-(1-imidazolyl)benzenemethanol

(49) α-(2,4,6-Trimethylphenyl)-2-amino-5-(1-imidazolyl)benzenemethanol

(50) α-(4-Chorophenyl)-2-(2-methyl-1-imidazolyl)-3-pyridinemethanol, melting at 203°–210° C.

(51) α-Phenyl-2-(1-imidazolyl)-5-pyridinemethanol, melting at 144°–146° C.

(52) α-(4-Fluorophenyl)-2-(1-imidazolyl)-5-pyridinemethanol, melting at 133°–135° C.

(53) α-(4-Methylphenyl)-2-(1-imidazolyl)-5-pyridinemethanol, melting at 149°–150° C.

(54) α-(3,4-Dimethylphenyl)-2-(1-imidazolyl)-5-pyridinemethanol, melting at 139°–141° C.

(55) α-(4-Cyclohexylphenyl)-2-(1-imidazolyl)-5-pyridinemethanol, melting at 162°–163° C.

(56) α-(2,4,6-Trimelthylphenyl)-2-(1-imidazolyl)-3-pyridinemethanol hydrochloride, melting at 237°–238° C. (decomposition)

(57) α-(4-Methoxyphenyl)-2-(1-imidazolyl)-5-pyridinemethanol, melting at 116°–119° C.

(58) α-(2-Methoxy-5-methylphenyl)-2-(1-imidazolyl)-5-pyridinemethanol, melting at 141°–143° C.

(59) α-(2-Hydroxy-5-methylphenyl)-2-(1-imidazolyl)-5-pyridinemethanol, melting at 164°–166° C.

(60) α-(2-Methoxy-5-chlorophenyl)-2-(1-imidazolyl)-5-pyridinemethanol melting at 171°–172° C.

(61) α-(2,4-Dimethoxyphenyl)-2-(1-imidazolyl)-5-pyridinemethanol, melting at 138°–140° C.

(62) α-(2,5-Dimethoxyphenyl)-2-(1-imidazolyl)-5-pyridinemethanol, melting at 127°–129° C.

(63) α-(3,4-Dimethoxyphenyl)-2-(1-imidazolyl)-5-pyridinemethanol, melting at 154°–155° C.

(64) α-(4-Carboxyphenyl)-2-(1-imidazolyl)-5-pyridinemethanol, melting at 224°–228° C.

(65) α-(6-Methoxy-2-naphthyl)-2-(1-imidazolyl)-5-pyridinemethanol, semi-solid

| Elementary analysis: | | | |
|---|---|---|---|
| | C (%) | H (%) | N (%) |
| Found: | 72.73 | 5.11 | 12.95 |
| Calculated: | 72.49 | 5.17 | 12.68 |

(66) α-(2-Carboxymethoxy-5-methylphenyl-2-(1-imidazolyl)-5-pyridinemethanol, melting at 219°–220° C. (decomposition)

(67) α-(2-Dimethylaminoethoxy-5-methylphenyl)-b 2-(1-imidazolyl)-5-pyridinemethanol oxalate, melting at 157°–158° C. (decomposition)

(68) α-(4-Methoxycarbonylphenyl)-2-(1-imidazolyl)-5-pyridinemethanol, melting at 150° C.

(69) α-(4-Chlorophenyl)-2-(2-methyl-1-imidazolyl)-5-pyridinemethanol, melting at 106°–110° C.

(70) α-(4-Chlorophenyl)-5-(1-imidazolyl)-2-thiophenemethanol hydrochloride, melting at 176°–177° C.

(71) α-(2,4,6-Trimethylphenyl)-5-(1-imidazolyl)-2-furanmethanol, melting at 142°–144° C.

EXAMPLE 72

To a solution of 16.2 g of 2-methyl-5-(1-imidazolyl)-2',6'-dimethyl-4'-carboxybenzophenone and 2.1 g of sodium hydroxide in 113 ml of water is added 2.8 g of sodium borohydride, and the mixture is stirred at 70°–75° C. for 3 hours. After completion of the reaction, a small amount of an isoluble substance is filtered off from the warm mixture and the filtrate is adjusted to pH 4 with concentrated hydrochloric acid under stirring at 80°–90° C. The precipitated crystals are collected by filtration under reduced pressure and washed with water well. After drying, recrystallization from dimethylformamide gives 14.0 g of α-(2,6-dimethyl-4-carboxyphenyl)-2-methyl-5-(1-imidazolyl)benzenemethanol, melting at 310°–312° C. with decomposition.

EXAMPLE 73

To a suspension 19.8 g of α-(2,6-dimethyl-4-carboxyphenyl)-2-methyl-5-iodobenzenemethanol, 5.1 g of imidazole, 13.8 g of potassium carbonate and 120 ml of dimethylformamide are added 0.4 g of potassium fluoride and 0.4 g of copper powder, and the mixture is stirred at 135°–140° C. for 30 hours. After cooling, to the reaction mixture is added 240 ml of water and further 0.45 g of sodium sulfide trihydrate. The whole mixture is stirred for 30 minutes. The precipitated copper sulfide is filtered with sellaite under reduced pressure and the filtrate is adjusted to pH 4 with concentrated hydrochloric acid under heating and stirring. The precipitated crystals are collected by filtration, washed with water and dried. Recrystallization from dimethylformamide gives α-(2,6-dimethyl-4-carboxyphenyl)-2-methyl-5-(1-imidazolyl)benzenemethanol, melting at 309°–311° C. with decomposition in high yield.

EXAMPLE 74

9.8 g of sodium hydroxide is dissolved in 750 ml of ethanol under heating and a small amount of an insoluble substance is filtered off. To the filtrate is added 75 g of α-(2,6-dimethyl-4-carboxyphenyl)-2-methyl-5-(1-imidazolyl)benzenemethanol, and the mixture is stirred at 70° C. for 30 minutes. After cooling, the precipitated crystals are collected by filtration under reduced pressure and washed with ethanol well. After drying at 60°–70° C. for 2–3 hours, the crystals are allowed to stand at room temperature for 2–3 days to give the corresponding sodium salt dihydrate, melting at 271°–285° C. as yellow crystals.

EXAMPLE 75

To a suspension of 20 g of α-(2,6-dimethyl-4-carboxyphenyl)-2-methyl-5-(1-imidazolyl)benzenemethanol in 200 ml of water is added a solution of 8.7 g of concentrated sulfuric acid and 30 ml of water under stirring, and the mixture is heated. After the solution is filtered, the filtrate is gradually cooled. The precipitated crystals are collected by filtration under reduced pressure, and then washed with dilute sulfuric acid and acetone. After drying at 70° C. for 2 hours, the crystals are, allowed to stand at room temperature for 2–3 days to give 23 g of the corresponding hemisulfate monohydrate, melting at 249°–251° C. with decomposition as white needles.

The following compounds can be prepared in a similar manner:

(76) α-(2,6-dimethyl-4-carboxyphenyl)-2-methyl-5-(1-imidazolyl)benzenemethanol methanesulfonate, melting at 250°–252° C. with decomposition;

(77) α-(2,6-dimethyl-4-carboxyphenyl)-2-methyl-5-(1-imidazolyl)benzenemethanol hydrochloride, melting at 282°–283° C. with decomposition;

(78) α-(2,6-dimethyl-4-carboxyphenyl)-2-methyl-5-(1-imidazolyl)benzenemethanol lysinate hemihydrate, melting at 168°–171° C.

EXAMPLE 79

To a solution of 6.4 g of 2-chloro-5-(1-imidazolyl)-2',6'-dimethyl-4'-carboxybenzophenone and 0.8 g of sodium hydroxide in 35 ml of water is added 1.4 g of sodium borohydride, and the mixture is stirred at 70°–75° C. for 3 hours. After completion of the reaction, a small amount of an insoluble substance is filtered off from the warm mixture and the filtrate is adjusted to pH 4 with concentrated hydrochloric acid under stirring at 80°–90° C. The precipitated crystals are collected by filtration under reduced pressure, washed with water and acetone and dried to give 6.1 g of α-(2,6-dimethyl-4-carboxyphenyl)-2-chloro-5-(1-imidazolyl)benzenemethanol, melting at 317°–320° C. with decomposition as white crystals.

EXAMPLE 80

To a suspension of 21 g of α-(2,6-dimethyl-4-carboxyphenyl)-2-chloro-5-iodobenzenemethanol, 5.1 g of imidazole, 13.8 g of potassium carbonate and 120 ml of dimethylformamide are added 0.4 g of potassium fluoride and 0.4 g of copper powder, and the mixture is stirred at 135°–140° C. for 30 hours. After cooling, to the reaction mixture is added 240 ml of water and 0.45 g of sodium sulfide trihydrate. The whole mixture is stirred for 30 minutes. The precipitated copper sulfide is filtered with sellaite under reduced pressure and the filtrate is adjusted to pH 4 with concentrated hydrochloric acid under heating and stirring. The precipitated crystals are collected by filtration, washed with water and then dried. Recrystallization from dimethylformamide gives α-(2,6-dimethyl-4-carboxyphenyl)-2-chloro-5-(1-imidazolyl)benzenemethanol, melting at 318°–320° C. with decomposition, as white crystals in high yield.

The following compounds can also be prepared:

(81) α-(2,6-dimethyl-4-ethoxycarbonylphenyl)-2-methyl-5-(1-imidazolyl)benzenemethanol, melting at 118°–119° C.; and its hydrochloride, melting at 241°–243° C. with decomposition;

(82) α-(2,6-dimethyl-4-isopropoxycarbonylphenyl)-2-methyl-5-(1-imidazolyl)benzenemethanol, melting at 193°–194° C.; and

(83) α-(2,6-dimethyl-4-methoxycarbonylphenyl)-2-methyl-5-(1-imidazolyl)benzenemethanol, melting at 168°–169° C.

FORMULATION EXAMPLE 25 mg tablets are prepared from the following composition:

| | |
|---|---|
| Compound of Example 3 | 25.0 mg |

| | |
|---|---|
| Lactose | 70.0 mg |
| Starch | 10.0 mg |
| Microcrystalline cellulose | 10.5 mg |
| Talc | 4.0 mg |
| Magnesium stearate | 0.5 mg |
| | 120.0 mg |

These tablets can be film-coated or sugar-coated, if desired. Further, capsules can be prepared by filling the above composition in a soft capsule.

Although this invention has been adequately discussed in the foregoing specification and examples included therein, various changes and modifications may be made without departing from the spirit and scope thereof.

What is claimed is:

1. A compound selected from the group consisting of α-(2,6-dimethyl-4-carboxyphenyl)-2-methyl-5-(1-imidazolyl) benzenemethanol, a pharmaceutically acceptable metal salt thereof, a pharmaceutically acceptable acid addition salt thereof, a hydrate thereof, and a mixture of at least two of said compounds.

2. A compound of claim 1, wherein the pharmaceutically acceptable acid addition salt is a pharmaceutically acceptable amino acid addition salt.

3. The compound of claim 1, namely α-(2,6-dimethyl-4-carboxyphenyl)-2-methyl-5-(1-imidazolyl)benzenemethanol sodium salt dihydrate.

* * * * *